United States Patent
Martin et al.

(10) Patent No.: US 9,642,580 B2
(45) Date of Patent: May 9, 2017

(54) MONITORING DEVICE INCLUDING COMPLIANT VARIABLE CAPACITOR FOR RESPIRATION AND CARDIAC SENSING APPLICATIONS

(71) Applicant: General Electric Company, Schenectady, NY (US)

(72) Inventors: Byron Patrick Martin, Waukesha, WI (US); Adam Gregory Pautsch, Waukesha, WI (US); Jesil Surendra Pujara, Madison, WI (US); William John Bonneau, Waukesha, WI (US)

(73) Assignee: General Electric Company, Schenectady, NY (US)

( * ) Notice: Subject to any disclaimer, the term of this patent is extended or adjusted under 35 U.S.C. 154(b) by 21 days.

(21) Appl. No.: 14/836,204

(22) Filed: Aug. 26, 2015

(65) Prior Publication Data
US 2017/0055921 A1 Mar. 2, 2017

(51) Int. Cl.
*A61B 5/00* (2006.01)
*A61B 5/11* (2006.01)
*A61B 5/113* (2006.01)

(52) U.S. Cl.
CPC .......... *A61B 5/7289* (2013.01); *A61B 5/1102* (2013.01); *A61B 5/1135* (2013.01); *A61B 5/6823* (2013.01); *A61B 5/6831* (2013.01); *A61B 5/6832* (2013.01); *A61B 5/7278* (2013.01); *A61B 2562/0214* (2013.01); *A61B 2562/04* (2013.01)

(58) Field of Classification Search
None
See application file for complete search history.

(56) References Cited

U.S. PATENT DOCUMENTS

| | | | |
|---|---|---|---|
| 3,760,794 | A | 9/1973 | Basham |
| 6,809,462 | B2 | 10/2004 | Pelrine et al. |
| 7,641,618 | B2 | 1/2010 | Noda et al. |
| 8,155,729 | B1 | 4/2012 | Hsieh et al. |

(Continued)

FOREIGN PATENT DOCUMENTS

| | | | |
|---|---|---|---|
| WO | 2009/050702 A2 | 4/2009 | |
| WO | 2011/054548 A1 | 5/2011 | |
| WO | WO2011147414 | * | 12/2011 |

OTHER PUBLICATIONS

"Fabric Sensor Evaluation Kit Datasheet", Stretchsense, May 2015.

*Primary Examiner* — Brian T Gedeon
(74) *Attorney, Agent, or Firm* — Andrus Intellectual Property Law, LLP (57) ABSTRACT

A monitoring device for obtaining data from a patient during a respiratory and/or cardiac cycle of the patient. The monitoring device includes a compliant variable capacitor securely attached to the patient. The capacitance of the compliant variable capacitor changes during movement of the patient caused by the respiratory cycle and/or a cardiac cycle. The changing capacitance is used to generate a monitoring signal that includes the frequency, timing and amplitude of either the respiratory or cardiac cycle. The signal from the monitoring device is provided to a medical imaging system such that the medical imaging system can compensate for the motion of the patient during the reparatory/cardiac cycle.

17 Claims, 8 Drawing Sheets

(56) References Cited

U.S. PATENT DOCUMENTS

| | | |
|---|---|---|
| 8,391,573 B2 | 3/2013 | Wollenweber |
| 8,449,471 B2 | 5/2013 | Tran |
| 2008/0000304 A1 | 1/2008 | Nagle et al. |

* cited by examiner

MONITORING DEVICE INCLUDING COMPLIANT VARIABLE CAPACITOR FOR RESPIRATION AND CARDIAC SENSING APPLICATIONS

BACKGROUND

The present disclosure generally relates to a method and system for monitoring the respiratory or cardiac cycles of a subject. More specifically, the present disclosure relates to a device that is able to discern the cardiac or respiratory cycles of a patient which can be used to monitor respiration to generate a triggering signal for use with a medical imaging system or in other applications.

Multi-modality medical imaging systems exist that scan using different modalities, for example, Computed Tomography (CT), Magnetic Resonance Imaging (MRI), Positron Emission Tomography (PET), and Single Photon Emission Computed Tomography (SPECT). During operation, the image quality of the conventional imaging systems may be affected by the motion of the object being imaged. In particular, motion of the imaged object can produce artifacts that degrade the image quality. More specifically, image artifacts are produced by movement of the object during image acquisition. Respiratory motion is a common source of involuntary motion in patients encountered in medical imaging systems. The respiratory motion may lead to errors during image review, such as when a physician is determining the size of a lesion, determining the location of the lesion, or quantifying the lesion.

One known method for reducing the imaging artifacts is to sort the image data into a plurality of gates based on a respiratory signal. One of the gates is then selected as the reference gate and the remaining gates are then registered to the reference gate. For example, the reference gate selected typically includes information that is collected at the end of the patient's breathing cycle. However, the reference gate having information collected at the end of the patient's breathing cycle may not include optimal information for registering the remaining gates. For example, the reference gate having information collected at the end of the patient's breathing cycle may not include a fewer number of pixels or pixels having a reduced pixel intensity. Thus, when the remaining gates are registered with the reference gate, the quality of the resultant image may be reduced.

In order for gating to be used with a medical imaging system, a triggering signal must be acquired from the patient that is related to the respiratory movement of the patient. Technologies currently exist to provide such a triggering signal. However, existing technologies are expensive, large, and bulky and in some instances difficult and time consuming to properly set up on the patient and are potentially uncomfortable for the patient to wear for extended periods. For this reason, a need exists for a small, unobtrusive, cost-effective monitoring device that is easy to use by both the clinician and the patient, improves workflow rates with respect to the medical imaging, system, improves performance and is comfortable for the patient.

SUMMARY

The present disclosure is directed to a method and system for acquiring a signal from a subject that is a measure of the respiratory or cardiac cycle of the subject. In one embodiment of the disclosure, the image data is acquired and synchronized with real-time motion data from a patient such that the acquired motion data can be used for motion compensation of the imaging data.

Motion data is acquired and synchronized with the image data from a medical imaging system. The motion data is acquired using a monitoring device that monitors the expansion and contraction of the thoracic or abdominal cavity of a patient. The monitoring device includes a movement sensor that is secured to the thoracic or abdominal cavity of the patient. During respiratory and/or cardiac cycles, the movement sensor generates a monitoring signal that indicates the frequency, timing and amplitude of the respiratory or cardiac cycle, which can then be used by the medical imaging system as a gating signal.

In accordance with one aspect of the present disclosure, the movement sensor includes a compliant variable capacitor that changes capacitance as the size, including both the thickness and the surface area, of the compliant variable capacitor changes. In an embodiment in which the compliant variable capacitor is an elongated strip, the capacitance changes as the length of the strip increases and/or as the thickness decreases. In an embodiment in which the compliant variable capacitor is applied directly to the patient, the capacitance changes as the surface area increases in a multi-directional manner, such as when the outer diameter of a circular compliant variable capacitor changes.

The monitoring device further includes a monitoring circuit that senses changes in the capacitance and generates the monitoring signal. The monitoring signal is indicative of the frequency, timing and amplitude of the expansion and contraction of the thoracic or abdominal cavity. The monitoring signal can be used in different applications and for different purposes, since the signal is representative of the full respiratory or cardiac cycle of the subject.

In accordance with one aspect of the disclosure, the movement sensor formed as part of the monitoring device includes a strap that surrounds the thoracic or abdominal cavity of the patient. As the thoracic cavity or abdominal cavity expands and contracts, the compliant variable capacitor, which is formed as part of the strap or attached to a flexible portion of the strap, expands and contracts at the same rate and proportional to the amplitude.

In accordance with another aspect of the disclosure, the compliant variable capacitor includes a dielectric elastomer that is located between two compliant electrodes. The dielectric and electrodes expand and contract with the patient and the change in capacitance of the dielectric is monitored by a monitoring circuit.

In yet another aspect of the present disclosure, the movement sensor can include a plurality of compliant variable capacitors that are connected to each other in parallel and are physically stacked on top of each other. The parallel connection of the compliant variable capacitors increases the sensitivity of the movement sensor, which can be desirable for monitoring cardiac cycles. In another aspect of the present disclosure, the movement sensor can be placed at another location on the patient, such as on a leg or neck, to monitor the pulse of the patient.

The present disclosure is further directed to a method of generating a triggering signal for use with a medical imaging system that includes attaching a movement sensor to a patient. The movement sensor includes a compliant variable capacitor that changes capacitance as the size of the compliant variable capacitor changes. The method monitors the changes in the capacitance of the compliant variable capacitor and converts the changes into a monitoring signal. The monitoring signal is used to determine the phase of the respiratory cycle when image data is obtained by the medical imaging system. The monitoring signal is synchronized with image data obtained by the medical imaging system. The medical imaging system can uses the synchronized monitoring signal as a gating signal to enhance the review of image data obtained by the medical imaging system. In accordance with the present disclosure, the compliant variable capacitor can be attached to the patient as part of a strap or by directly attaching the compliant variable capacitor to the patient with an adhesive.

Various other features, objects and advantages of the invention will be made apparent from the following description taken together with, the drawings.

BRIEF DESCRIPTION OF THE DRAWINGS

The drawings illustrate the best mode presently contemplated of carrying out the disclosure. In the drawings.

DETAILED DESCRIPTION

Figure 1:
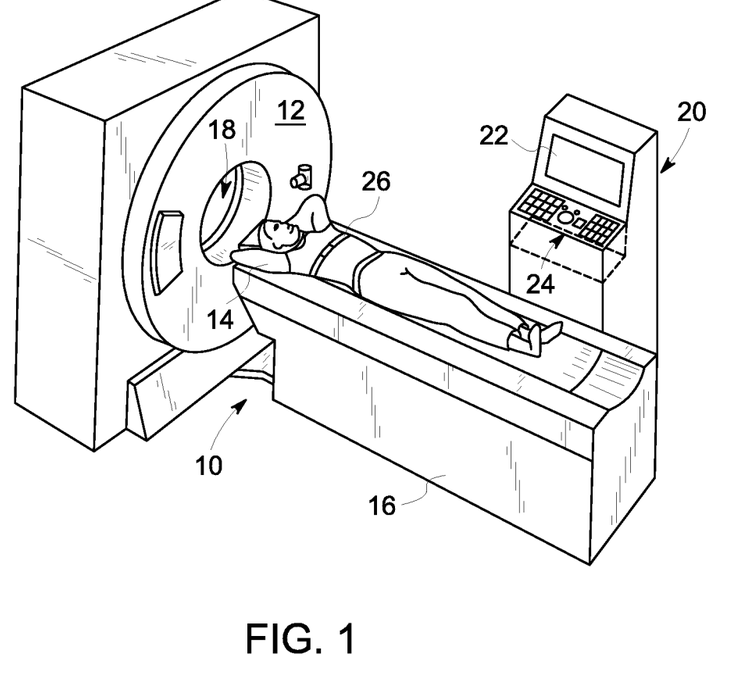
FIG. 1 is a pictorial perspective view of a medical imaging system utilizing the device of the present disclosure.

FIG. 1 illustrates a medical imaging system 10. In the embodiment illustrated, the medical imaging system is a CT scanner that includes a gantry 12 that has an X-ray source that projects a beam of X-rays toward a detector array on the opposite side of the gantry 12. The detector array senses the projected X-rays that pass through the patient 14. The patient 14 is supported on a table 16 that moves through an opening 18 during the scanning process.

Although the present disclosure is shown with the medical imaging system 10 comprising a CT scanner, the present disclosure is equally applicable with other image modalities. For example, the medical imaging system could be a combination PET/MR system or a stand-alone ultrasound and a stand-alone MR scanner that work in tandem to acquire motion and image data.

As illustrated in FIG. 1, the medical imaging system 10 includes a control station 20 having a display 22 and a user input device 24. A data acquisition system in the control station 20 samples data from the detectors within the scanner and converts the data into digital signals for subsequent processing. The present disclosure is directed to a method and apparatus for acquiring motion data from the patient for use in reviewing image data within the medical imaging system 10.

As shown in FIG. 1, the patient 14 is wearing a monitoring device 26 constructed in accordance with the present disclosure. The monitoring device 26 is shown in FIG. 1 as surrounding the thoracic cavity of the patient 14. However, the monitoring, device could also be positioned surrounding the abdominal cavity of the patient 14 or at any other location where movement of the patient is important.

Figure 2:
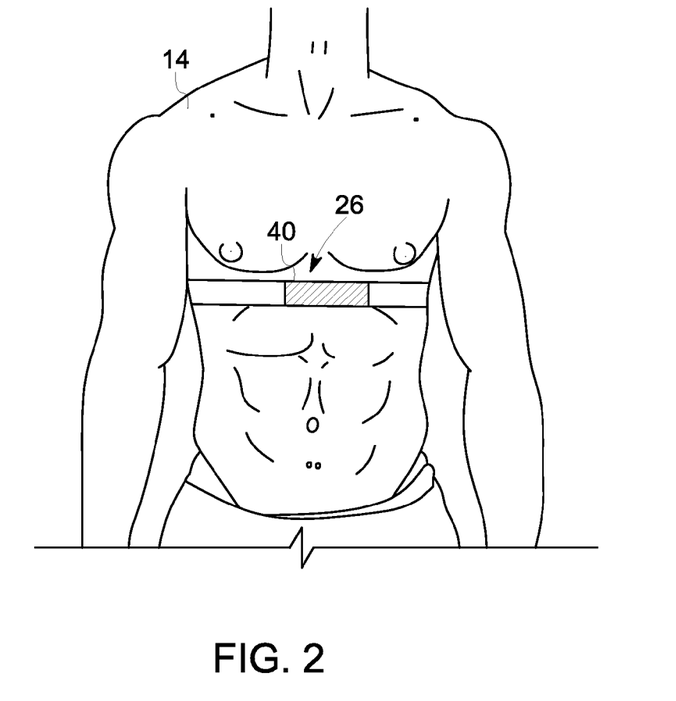
FIG. 2 is a front view of patient wearing the monitoring device of the present disclosure.
Figure 3:
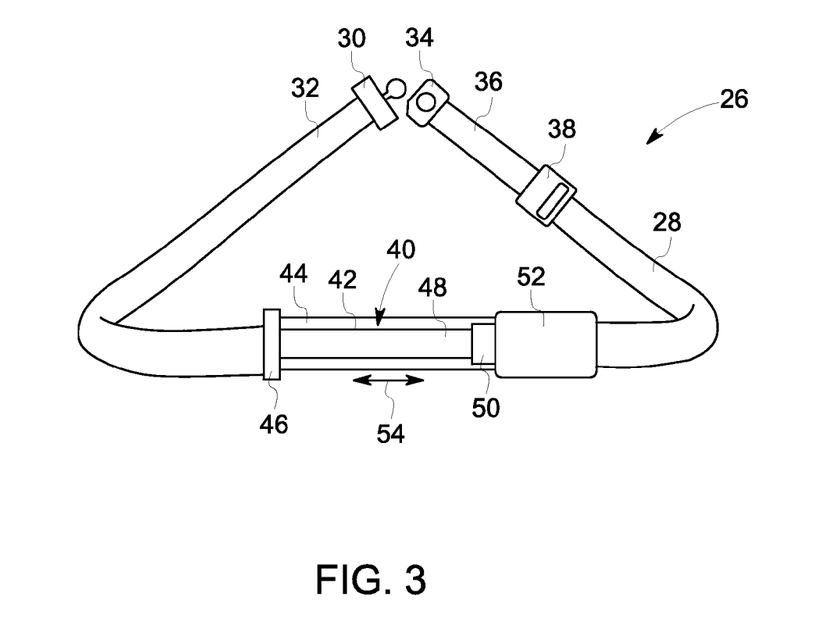
FIG. 3 is a perspective view of the monitoring device.

FIG. 2 provides an additional illustration of a patient 14 wearing a first embodiment of the monitoring device 26 of the present disclosure. The monitoring device 26 is shown surrounding the thoracic cavity of the patient, which can be used for monitoring the respiration cycles of the patient and/or cardiac cycles of the patient. The first embodiment of the monitoring device 26 is more clearly shown in FIG. 3. As shown in FIG. 3, the monitoring device 26 includes a strap 28 that includes a male connector 30 on a first end 32 and a female connector 34 on a second end 36. The strap 28 can be formed from different types of material that are comfortable when worn by the patient, such as but not limited to fabric or woven nylon. The strap 28 is preferably formed with a flexible section formed from an elastic material that, when positioned on the patient 14 as shown in FIG. 2, can expand and contract along with the expansion and contraction of the thoracic cavity of the patient during normal breathing cycles. The adjustment buckle 38 allows the length of the strap 28 to be adjusted such that the strap fits tightly around the thoracic cavity.

The monitoring device 26 further includes a movement sensor 40. The movement sensor 40 operates to generate a monitoring signal that is indicative of the movement of the chest cavity during the respiration cycle and/or movement of the chest cavity as a result of the cardiac cycle. The movement sensor 40 shown in FIG. 3 includes a compliant variable capacitor 42. The compliant variable capacitor 42 is a device that changes capacitance as the length and/or thickness of the compliant variable capacitor changes. In the embodiment shown in FIG. 3, the capacitor 42 takes the shape of an elongated strip that is aligned with a flexible portion of the strap and has a first end 44 secured to the strap 28 by a connector 46. A second end 48 of the compliant variable capacitor 42 is also fixed to the flexible portion of the strap. In the embodiment shown, the second end 48 includes a plug 50 that is received within an electronics housing 52. The electronics housing 52 is secured to the strap 28 such that both ends of the compliant variable capacitor are generally fixed to the strap 28. Although the electronics housing 52 is shown in the embodiment of FIG. 3, the electronics housing could be located in another position and the compliant variable capacitor 42 could be connected to the electronics by a cable of other wiring.

During movement of the thoracic cavity of the patient 14 during breathing, the length of the flexible portion of the strap 28, along with the compliant variable capacitor, expands and contracts at a frequency that corresponds to the respiratory cycle. The expansion and contraction is shown by arrow 54 in FIG. 3. During this expansion and contraction, the compliant variable capacitor 42 moves between a relaxed state shown in FIG. 3 and an extended state. During this movement, the capacitance of the compliant variable capacitor 42 changes. The changing capacitance is detected by operating components within the electronics housing 52 in a manner that will be described in greater detail below.

Although an electronics housing 52 is shown in FIG. 3, it is contemplated that the electronics housing 52 could be substantially reduced in size or eliminated depending upon the electronic components needed to operate the monitoring device 26 in the manner to be described in detail below. Additionally, the strap 28 could be formed from many different types of material as long as the physical configuration of the compliant variable capacitor 42 can change along with the respiratory cycle or cardiac cycle of the patient.

Figure 4:
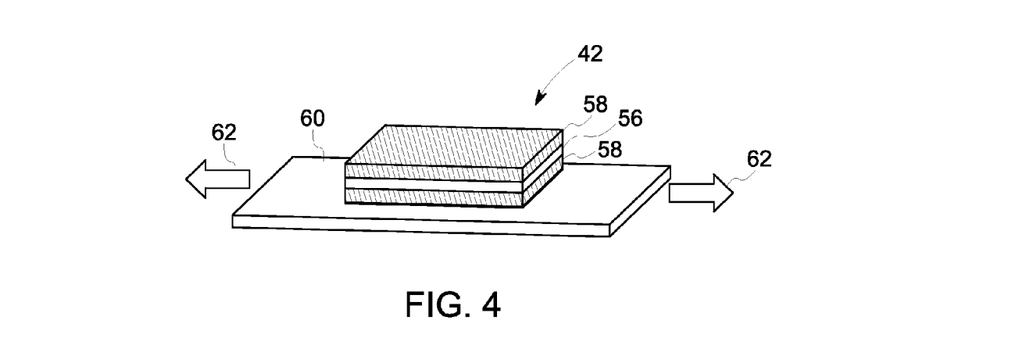
FIG. 4 is a perspective view of the movement sensor incorporated into the monitoring device in a relaxed state.
Figure 5:
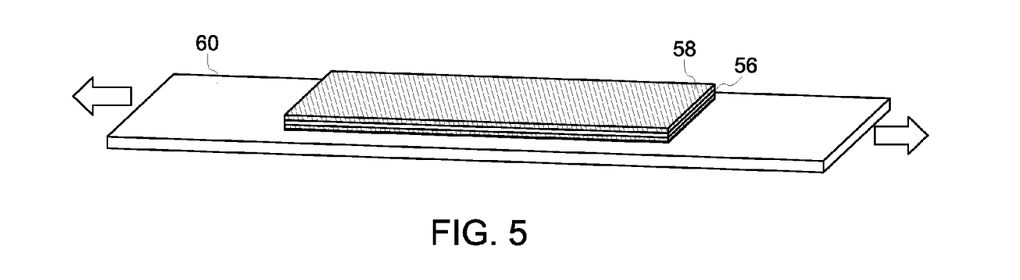
FIG. 5 is a view similar to FIG. 4 showing the movement sensor in an extended state.

Referring now to FIGS. 4 and 5, one embodiment of the compliant variable capacitor 42 is illustrated. In the embodiments shown, the capacitor 42 includes a dielectric elastomer 56 sandwiched between a pair of compliant electrodes 58. The pair of electrodes 58 and dielectric elastomer 56 is supported on a compliant substrate 60 by an adhesive or mechanical bond. The combination of the dielectric elastomer 56, the compliant electrodes 58 and the substrate 60 is able to stretch in the direction shown by arrows 62 into the extended state shown in FIG. 5. As can be seen in FIG. 5, the thickness of both of the electrodes 58 and the dielectric elastomer 56 are substantially reduced during stretching of the substrate 60. The capacitance of the dielectric elastomer 56 is represented by the equation:

$$C = \epsilon_r \epsilon_0 (A/d) \tag{Equation 1}$$

C: Capacitance
A: Surface area of capacitor
d: Elastomer thickness
$\epsilon_0$: Permittivity of free space
$\epsilon_r$: Relative static permittivity As can be understood by Equation 1, during stretching of the compliant variable capacitor 42, the surface area (A) increases and the dielectric elastomer thickness (d) decreases. During this process, the capacitance of the compliant variable capacitor 42 increases, which occurs during the thoracic/abdominal expansion due to respiration or the cardiac cycle. As an illustrated, but non-limiting example, during the un-stretched relaxed state, the capacitance (C) may be 330 pF while in the fully stretched state, the capacitance (C) will be 440 pF. In the embodiment illustrated, the compliant variable capacitor has a sensitivity of 1.38 pF/mm. By monitoring the change in the capacitance (C), an electronic monitoring circuit can detect the movement of the thoracic or abdominal cavity. The detected monitoring signal can then be used as a triggering signal that can be used in a variety of ways, such as for gating the medical imaging system 10, as will be described in greater detail below.

Figure 8:
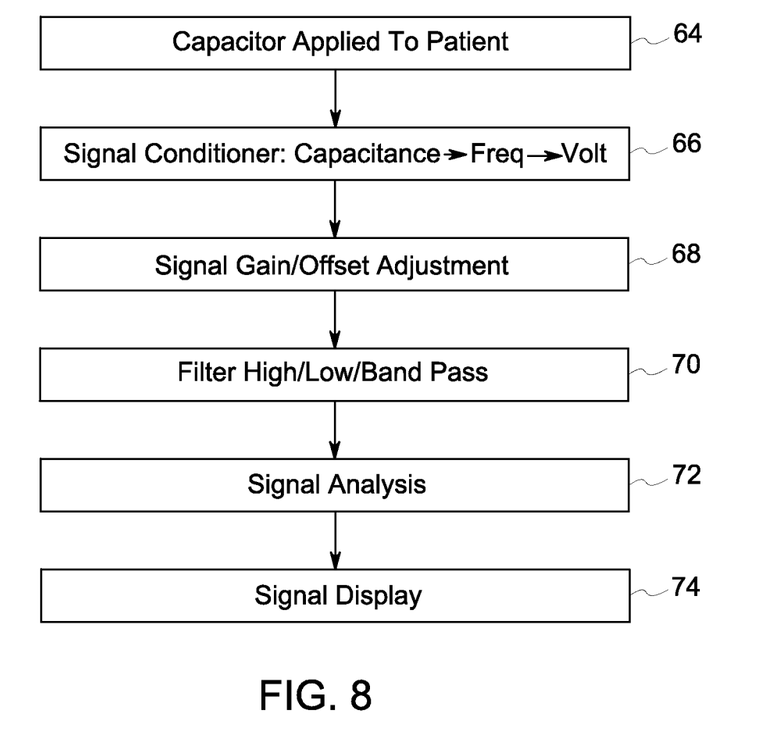
FIG. 8 is a flow chart illustrating the operation of the monitoring device.

Referring now to FIG. 8, representative steps that are used to monitor the changing capacitance of the movement sensor are shown and described in a flow chart. As illustrated in step 64, the capacitor is initially applied to the patient. In the embodiment shown and described in FIG. 2, the capacitor is applied to the patient utilizing the strap. However, other methods of attaching the capacitor to the patient, such as directly with an adhesive, are contemplated as being within the scope of the present disclosure.

The monitoring device 26 can be applied to the patient prior to the patient entering the scanning room that includes the medical imaging system. The ability to apply the monitoring device to the patient prior to entering the scanning room increases workflow, since the amount of time the patient needs to be in the scanning room is reduced. Once the scanning procedure is completed, the patient can be removed from the scanning room with the monitoring device still attached, which again increases workflow by reducing the time the patient is in the scanning room.

Once the capacitor and associated circuitry are applied to the patient, the operating circuitry applies an excitation signal, such as but not limited to a voltage, to the pair of electrodes positioned on the opposite sides of the dielectric material. As indicated previously in the discussion of FIGS. 4 and 5, as the substrate 60 stretches, the capacitance (C) changes. In step 66, a signal conditioner circuit changes the variable capacitance into a frequency, which is subsequently converted to a voltage. The signal conditioning circuit used to convert the changing capacitance to a voltage allows the system to further condition the signal. For example, the system can map the waveform of the breathing cycle to measure respiration rate and/or breathing amplitudes, which can be used for gating or as a measurement of respiration. In step 68, the value of the voltage signal is adjusted through either a gain or offset adjustment. Once the signal has been adjusted, the signal is sent through a filter in step 70 to reduce artifacts prior to transmission of the signal. In step 72, the signal can be analyzed and possibly displayed in step 74. The signal analysis shown in step 72 and the signal display step 74 can take place in multiple locations, such as within the control station of the medical imaging system.

Figure 6:
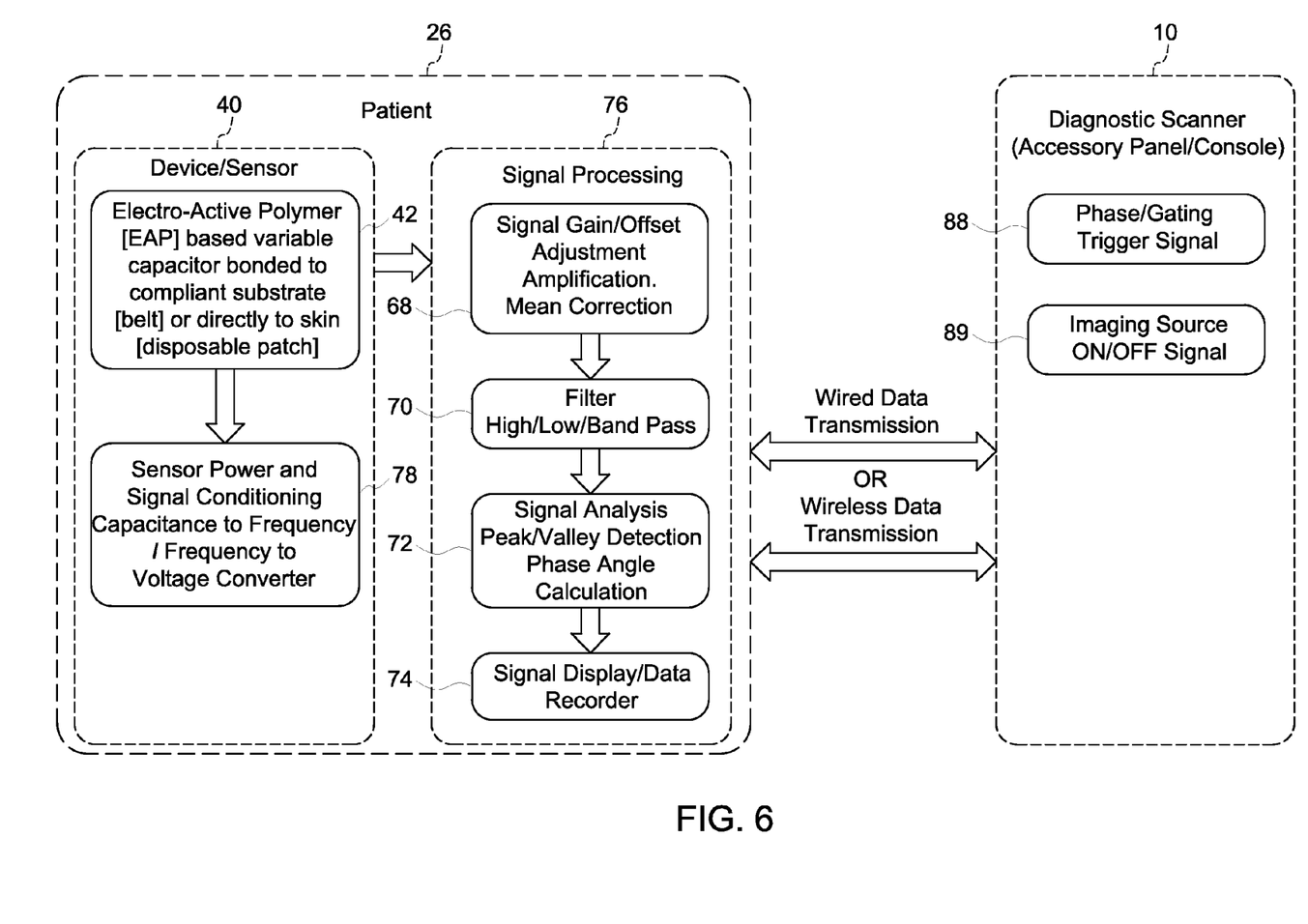
FIG. 6 is a schematic illustration showing the communication between the monitoring device and the medical imaging system.

FIG. 6 illustrates a first embodiment of the steps shown in FIG. 8. In the embodiment shown in FIG. 6, the monitoring device 26 includes both the movement sensor 40 as well as the signal processing components 76. In the embodiment shown in FIG. 6, the movement sensor 40 includes both the compliant variable capacitor 42 and signal conditioning circuitry 78. The signal conditioning circuitry 78 converts the variable capacitance into a signal which is the transferred to the signal processing circuitry 78. The signal processing circuitry 78 carries out various different processes shown by steps 68, 70, 72 and 74, which were previously described with reference to FIG. 8.

Once the signal processing has been carried out by the signal processing circuitry 78, data can be transferred from the monitoring device 26 to the medical imaging system 10 or can be displayed directly. In the embodiment shown in FIG. 6, the data can be transferred using either a wired data transmission path or a wireless data transmission path. It is contemplated that the wireless data transmission path could be one of many different types of wireless communication techniques, such as but not limited to the medical wireless band or Bluetooth in a non-medical application.

Figure 11:
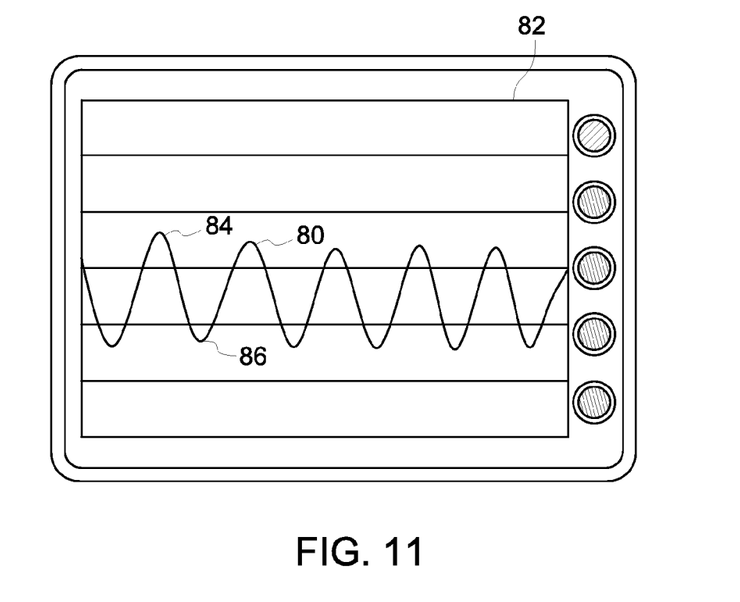
FIG. 11 is a representation of a display of the monitoring signal generated by the monitoring device.

FIG. 11 presents a representation of the monitoring signal 80 generated by the signal processing circuitry 76 and transmitted to the medical imaging system. The monitoring signal 80 is shown on a display 82. However, the monitoring signal could be simply transmitted to the medical imaging system 10 and not shown.

The monitoring signal 80 includes a series of peaks 84 and valleys 86 that represent the respiratory cycle of the patient. The peak 84 represents a fully extended, stretched condition of the compliant variable capacitor while the valley 86 represents a fully retracted, relaxed state of the compliant variable capacitor. Although the peaks and valleys are representative benchmarks of the signal 80, other benchmarks, such as changes in slope, zero crossings and maximum/minimum values, could be used as triggering events. The monitoring signal 80 thus represents the breathing rate and amplitude of the breathing cycle of the patient. As described previously, the frequency of the respiratory cycle can be used within the medical imaging system 10 for many different purposes, such as for gating medical images.

In addition to using the monitoring signal with a medical imaging system, the signal can be used in many different applications in which the frequency and/or timing of the respiratory or cardiac cycle are useful. Such applications do not need to be limited to the medical environment, but could also include in-home monitoring devices or personal fitness devices.

FIG. 6 illustrates the use of the monitoring signal 80 as a phase/gating trigger signal in block 88 and as an on/off signal in block 89. By utilizing the monitoring device 26 of the present disclosure, the medical imaging system 10 is able to obtain a gating signal through expansion and contraction of the compliant variable capacitor contained within the movement sensor.

Figure 7:
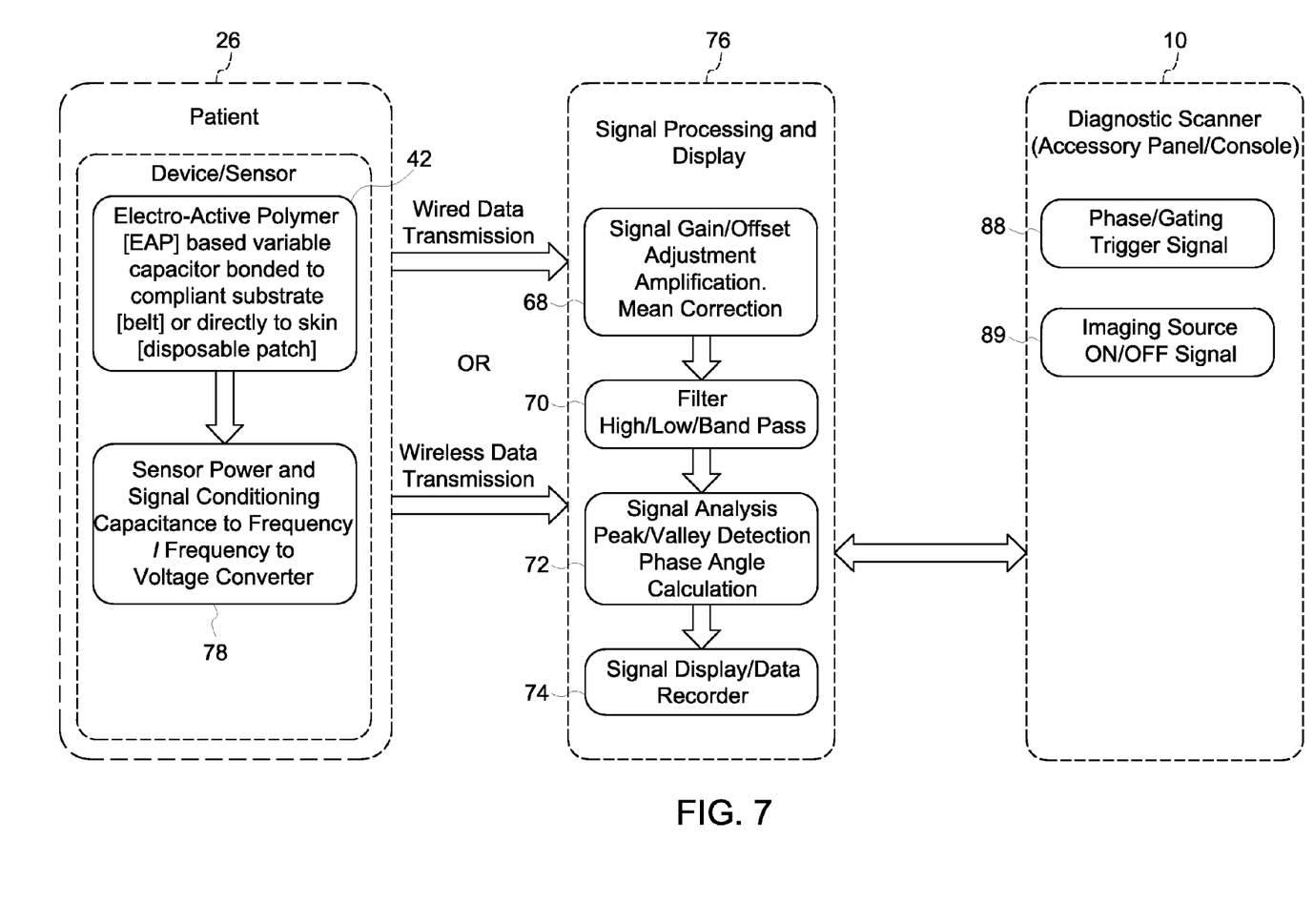
FIG. 7 is a schematic illustration similar to FIG. 6 with the processing separate from the monitoring device.

FIG. 7 illustrates an alternate embodiment of the configuration shown in FIG. 6. In the embodiment of FIG. 7, the monitoring device 26 applied to the patient does not include the signal processing circuitry 76. Instead, this circuitry is contained within a separate device, which may be part of the medical imaging system or as a separate device located in the vicinity of the patient. In the embodiment shown in FIG. 7, the monitoring device 26 transmits data from the signal conditioning circuitry 78 to the signal processing circuitry utilizing either wired data transmission techniques or wireless data transmission techniques. It is contemplated that the wireless data transmission technique would be used in a preferred embodiment and in such an embodiment, the wireless technique would be using the medical wireless band or Bluetooth. However, other types of wireless data transmission techniques are contemplated as being within the scope of the present disclosure. In the embodiment shown in FIG. 7, the signal processing circuitry 76 could be part of the medical imaging system 10 and thus would reduce the cost and complexity of the monitoring device 26 applied to the patient.

Figure 9:
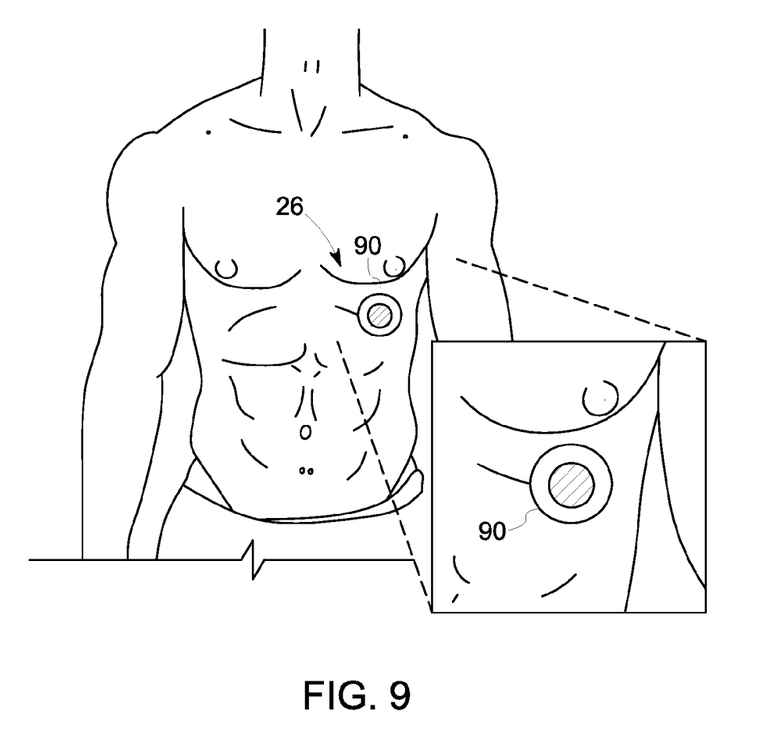
FIG. 9 is a first alternate embodiment of the monitoring device shown applied to a patient.

FIG. 9 illustrates a second, alternate embodiment of the monitoring device 26. In the embodiment shown in FIG. 9, the monitoring device takes the firm of a patch that can be attached directly to the patient, such as by an adhesive. In the embodiment shown, the patch 90 has a circular shape and is applied to the patient anywhere along the thoracic cavity. Although a circular patch is shown, it is contemplated that the patch 90 could have any shape that can expand/contract omni-directionally while operating within the scope of the present disclosure. The patch 90 has a generally similar cross-sectional configuration as the compliant variable capacitor 42 shown in FIGS. 4 and 5. Specifically, the patch 90 includes a dielectric elastomer positioned between two compliant electrodes.

Figure 10:
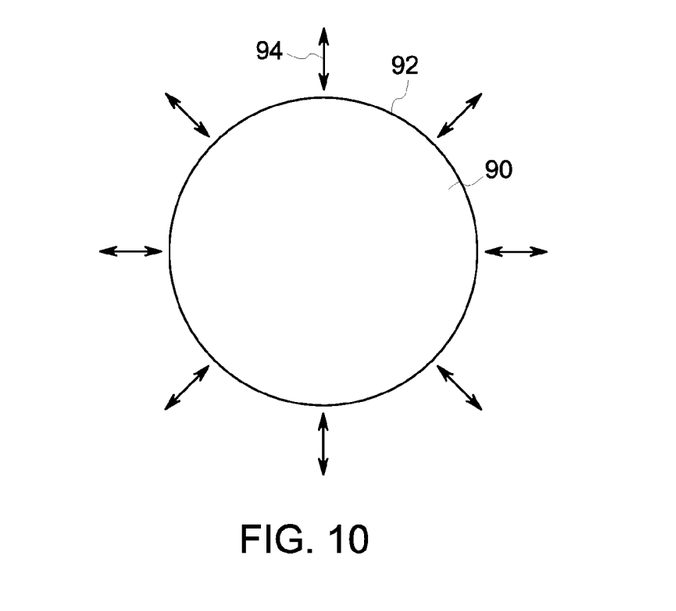
FIG. 10 is a magnified view of the second embodiment of the movement sensor.

Referring now to FIG. 10, during the respiratory cycle, the expansion and contraction of the chest cavity causes the patch 90 to expand in omni-directions, which increases the surface area of the dielectric and decreases the thickness of the dielectric. In the embodiment shown, the outer diameter 92 of the circular patch 90 expands and contracts as shown by arrows 94. The change in capacitance of the patch 90 is represented by Equation 1 and is related to the surface area of the patch 90 divided by the thickness of the elastomer.

It is contemplated that the embodiments shown in FIGS. 9 and 10 could be a disposable patch and the configuration provides the advantage of allowing the patch to be applied in any orientation relative to the direction of expansion of the chest cavity.

Figure 12:
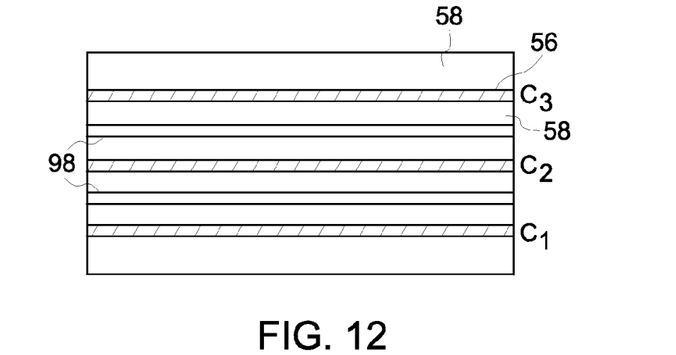
FIG. 12 is second, alternate embodiment of the movement sensor.
Figure 13:
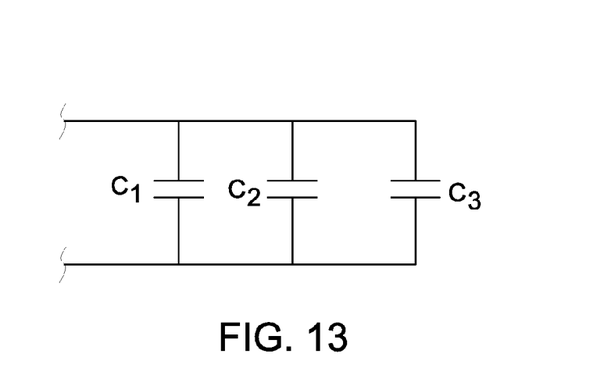
FIG. 13 is a schematic illustration of the embodiment shown in FIG. 12.

FIG. 12 illustrates another alternate embodiment for the movement sensor. In the embodiment shown in FIG. 12, three separate variable capacitors $C_1$, $C_2$ and $C_3$ are shown stacked on top of each other. Each of the compliant variable capacitors includes the dielectric elastomer layer 56 and a pair of spaced electrodes 58. A compliant insulation layer 98 is located between each of the stacked capacitors to electrically separate the capacitors at their physical boundary. As illustrated in FIG. 13, each of the individual capacitors $C_1$, $C_2$ and $C_3$ are connected to each other in parallel. In such an embodiment, the total capacitance is equal to the sum of the individual capacitive layers. By stacking the individual capacitors as shown in FIGS. 12 and 13, the capacitance change due to the stretching of the compliant variable capacitor is effectively multiplied, which increases the sensitivity to movements of the patient. Such a stacked capacitor may be used when the monitoring device is attempting to monitor the cardiac cycle of a patient, since the cardiac cycle results in much smaller movements of either the thoracic or the abdominal cavity. The stacked capacitor shown in FIG. 12 can be formed in many different ways, such as simply stacking capacitors or by rolling a single capacitor to form multiple layers.

In another embodiment, since the pulse of a patient can be sensed by expansion and contraction of blood vessels through the skin, it is contemplated that the monitoring device of the present disclosure could be placed at a location on the patient to sense the heartbeat of the patient. In such an embodiment, the monitoring device would be positioned on the neck or leg of the patient to obtain the signal from the carotid or femoral artery.

Although not shown in the drawing Figures, it is contemplated that the compliant variable capacitor could be embedded in a close-fitting garment worn between the upper shoulders and the waist of a patient, such as T-shirt or tank top, of either solid construction or fitted with some means to facilitate putting on the garment easily. In such an embodiment, the compliant variable capacitor would be able to stretch and retract in synchronization with the respiratory cycle of the patient.

In yet another contemplated embodiment, the compliant variable capacitor could be integrated into the patient table or bed such that a portion of the compliant variable capacitor would stretch and retract again in synchronization with the respiratory cycle of the patient.

In yet another enhancement, it is contemplated that the monitoring device may be equipped with some type of feedback to indicate that the device has established communication with the data acquisition system and is properly and securely attached to the patient and accurately detecting movement to be used as a gating reference. The feedback to the user could be a visual, audio or haptic feedback signal.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

We claim:

1. A device for monitoring expansion and contraction of a thoracic or abdominal cavity of a patient, comprising:
   a movement sensor secured to the thoracic or abdominal cavity, wherein the movement sensor includes a plurality of compliant variable capacitors that each change capacitance as the thoracic or abdominal cavity expands and contracts, wherein the plurality of variable capacitors are positioned on top of each other and electrically connected in parallel; and a monitoring circuit that senses the changing capacitance in the parallel connected plurality of variable capacitors and generates a monitoring signal that indicates the expansion and contraction of the thoracic or abdominal cavity.

2. The device of claim 1 wherein the movement sensor is formed as part of a strap that surrounds the thoracic or abdominal cavity of the patient.

3. The device of claim 1 wherein the movement sensor is attachable to the patient by an adhesive.

4. The device of claim 3 wherein the compliant variable capacitors expand and contract in omni-directions.

5. The device of claim 1 wherein each of the compliant variable capacitors includes a dielectric elastomer located between two electrodes.

6. The device of claim 1 further comprising a wireless transceiver coupled to the monitoring circuit to wirelessly transmit the monitoring signal from the device.

7. The device of claim 1 wherein the monitoring signal is indicative of a breathing cycle of the patient.

8. The device of claim 1 wherein the monitoring signal is indicative of a cardiac cycle of the patient.

9. A method of generating a monitoring signal representative of a respiratory and/or cardiac cycle of a patient, comprising the steps of:

attaching a movement sensor to a patient, the movement sensor including a plurality of compliant variable capacitors that each change capacitance as the size of the compliant variable capacitors change during the respiratory and/or cardiac cycle of the patient, wherein the plurality of variable capacitors are positioned on top of each other and electrically connected in parallel;

monitoring the changes in the capacitance of the plurality of parallel connected compliant variable capacitors; and converting the changes in the capacitance into a monitoring signal that represents the respiratory and/or cardiac cycle of the patient.

10. The method of claim 9 further comprising the steps of:
transmitting the monitoring signal to a medical imaging system; and
utilizing the monitoring signal to relate the respiratory and/or cardiac cycle to an output of the medical imaging system.

11. The method of claim 10 wherein movement sensor is applied to the patient prior to the patient being transferred to a scanning room including the medical imaging system.

12. The method of claim 9 wherein the compliant variable capacitors are attached to the patient as part of a strap that surrounds the thoracic or abdominal cavity of the patient.

13. The method of claim 9 wherein the movement sensor is attached to the patient by an adhesive.

14. The method of claim 9 wherein each of the compliant variable capacitors includes a dielectric elastomer located between two electrodes.

15. A device for monitoring expansion and contraction of a thoracic cavity or abdominal cavity of a patient for use with a medical imaging system, comprising:

a movement sensor secured to the thoracic or abdominal cavity of the patient, wherein the movement sensor includes a plurality of compliant variable capacitors positioned on top of each other and electrically connected in parallel, each capacitor including a dielectric elastomer located between two electrodes, wherein the capacitance of the dielectric elastomer changes as a surface area and/or a thickness of the dielectric elastomer changes;

a monitoring circuit that detects the changes in the capacitance of the dielectric elastomer and generates a monitoring signal; and a transceiver coupled to the monitoring circuit to transmit the monitoring signal from the device to the medical imaging system.

16. The device of claim 15 wherein the movement sensor is formed as part of a strap that surrounds the thoracic or abdominal cavity of the patient.

17. The method of claim 15 wherein the monitoring signal represents the frequency, timing and amplitude of either a respiratory or cardiac cycle of the patient.

* * * * *